US007947440B2

(12) United States Patent
Stroot et al.

(10) Patent No.: US 7,947,440 B2
(45) Date of Patent: **\*May 24, 2011**

(54) METHOD FOR DETERMINING THE SPECIFIC GROWTH RATE OF A DISTINCT CELL POPULATION WITHIN A NON-HOMOGENEOUS SYSTEM

(75) Inventors: Peter George Stroot, Lutz, FL (US); Matthew Raymond Cutter, Tampa, FL (US)

(73) Assignee: University of South Florida, Tampa, FL (US)

( * ) Notice: Subject to any disclaimer, the term of this patent is extended or adjusted under 35 U.S.C. 154(b) by 20 days.

This patent is subject to a terminal disclaimer.

(21) Appl. No.: 11/521,765

(22) Filed: Sep. 15, 2006

(65) Prior Publication Data

US 2010/0261161 A1    Oct. 14, 2010

Related U.S. Application Data

(60) Provisional application No. 60/718,078, filed on Sep. 16, 2005.

(51) Int. Cl.
*C12Q 1/68* (2006.01)
*C12P 19/34* (2006.01)
*C12N 1/12* (2006.01)
*C12N 1/20* (2006.01)
*C07H 21/02* (2006.01)
*C07H 21/04* (2006.01)

(52) U.S. Cl. ..... 435/6; 435/91.2; 435/252.1; 435/252.4; 435/252.7; 435/252.8; 536/23.1; 536/24.3

(58) Field of Classification Search .......... None
See application file for complete search history.

(56) References Cited

U.S. PATENT DOCUMENTS 5,712,095 A    1/1998    Britschgi et al.
5,726,021 A    3/1998    Britschgi et al.
5,770,373 A    6/1998    Britschgi et al.

OTHER PUBLICATIONS

Noordhoek, G.T. et al., J. Clin. Microbiol., vol. 32, pp. 277-284 (1994).*
Cox, R.A., Microbiology, vol. 150, pp. 1413-1426 (May 2004).*
Felske, A. et al., Appl. Env. Microbiol., vol. 64, pp. 4581-4587 (1998).*
Licht, T. R. et al., Env. Microbiol., vol. 1, pp. 23-32 (1999).*
Ashelford, K.E. et al. "PRIMOSE: a computer program for generating and estimating the phylogenetic range of 16S rRNA oligonucleotide probes and primers in conjunction with the RDP-II database", *Nucleic Acids Research*, 2002, 30(15):3481-3489.
Cangelosi, G.A. et al. "Depletion of Pre-16S rRNA in Starved *Escherichia coli* Cells", *J. Bacteriol.*, 1997, 179:4457-4463.
Cannon, M. et al. "A Comparative Study on the Inhibitory Actions of Chloramphenicol, Thiamphenicol and Some Fluorinated Derivatives", *J. Antimicrobial Chemotherapy*, 1990, 26:307-317, abstract.
Drainas, D. et al. "Aminoacyl Analogs of Chloramphenicol: Examination of the Kinetics of Inhibition of Peptide Bond Formation", *J. Med. Chem.*, 1993, 36:3542-3545.
Garcia-Martinez, J. et al. "RISSC: a novel database for ribosomal 16S-23S RNA genes spacer regions", *Nucleic Acids Res.*, 2001, 29(1):178-80.
Gausing, K. "Regulation of ribosome production in *Escherichia coli*: synthesis and stability of ribosomal RNA and of ribosomal protein messenger RNA at different growth rates" *J. Mol. Biol.*, 1977, 115(3):335-54.
Loy, A. et al. "probeBase: An Online Resource for rRNA-Targeted Oligonucleotide Probes" *Nucleic Acids Res.*, 2003, 31(1):514-6.
Mateus, C.R. et al "An Alternative Approach to Aminodiols from Baylis-Hillman Adducts. Stereoselective Synthesis of Chloramphenicol, Fluoramphenicol and Thiamphenicol", *Chem. Soc.*, 2005, 16(3A):386-396.
McFarlan, S.C. et al. "Inhibition of peptidyltransferase and possible mode of action of a dipeptidyl chloramphenicol analog" *Biochem. Biophys. Res. Commun.*, 1984, 122:748-754, abstract.
Michelinaki, M. et al. "Aminoacyl and Peptidyl Analogs of Chloramphenicol as Slow-Binding Inhibitors of Ribosomal Peptidyltransferase: A New Approach for Evaluating Their Potency", *Molecular Pharmacology*, 1997, 51:139-146.
Oerther, D.B. et al. "Monitoring Precursor 16S rRNAs of *Acinetobacter* spp. in Activated Sludge Wastewater Treatment Systems", *Appl. Environ. Microbiol.*, 2000, 66:2154-2165.
Stroot, P.G. "Novel transcription method confirms growth inhibition of bacteria exposed to domestic wastewater" Ph.D. Dissertation, University of Cincinnati, 2004.
Stroot, P.G. et al. "Elevated Precursor 16S rRNA Levels Suggest the Presence of Growth Inhibitors in Wastewater", *Water Sci. Technol.*, 2003, 47(11):241-250.
Tomlins, R.I. et al. "Precursor Ribosomal Ribonucleic Acid and Ribosome Accumulation In Vivo During the Recovery of *Salmonella typhimurium* from Thermal Injury", *J. Bacteriol.*, Jul. 1971, 107(1):134-42.
Vince, R. et al. "Choramphenicol Binding Site with Analogues of Chloramphenicol and Puromycin", *Antimicrobial Agents and Chemotherapy*, 1975, 8(4):439-443.

* cited by examiner

*Primary Examiner* — Teresa E Strzelecka
(74) *Attorney, Agent, or Firm* — Saliwanchik, Lloyd & Eisenschenk

(57) ABSTRACT

The present invention provides a method for measuring the specific rate of ribosome synthesis for a distinct cell population, such as a distinct microbial population. For an actively growing (or non-growing) culture, the specific rate of ribosome synthesis is identical to the specific growth rate of the culture. With the method of the invention, researchers will be able to measure the specific growth rate of distinct cell populations in mixed cultures, such as biological reactor systems or environmental samples. In addition, the method of the invention provides the ability to identify members of a distinct cell population that are rapidly growing.

16 Claims, 3 Drawing Sheets

SEQUENCE LISTING

```
<160> NUMBER OF SEQ ID NOS: 2

<210> SEQ ID NO 1
<211> LENGTH: 18
<212> TYPE: DNA
<213> ORGANISM: Acinetobacter calcoaceticus

<400> SEQUENCE: 1
gctgcctccc gtaggagt                                                 18

<210> SEQ ID NO 2
<211> LENGTH: 24
<212> TYPE: DNA
<213> ORGANISM: Acinetobacter calcoaceticus

<400> SEQUENCE: 2
ctggaattct accatcctct ccca                                          24
```

METHOD FOR DETERMINING THE SPECIFIC GROWTH RATE OF A DISTINCT CELL POPULATION WITHIN A NON-HOMOGENEOUS SYSTEM

CROSS-REFERENCE TO RELATED APPLICATION

The present application claims the benefit of U.S. Provisional Application Ser. No. 60/718,078, filed Sep. 16, 2005, which is hereby incorporated by reference herein in its entirety, including any figures, tables, nucleic acid sequences, amino acid sequences, and drawings.

BACKGROUND OF THE INVENTION

Microbiologists have used the spectrophotometer to measure the specific growth rate of pure cultures of microbes (e.g., bacteria) for over fifty years. For mixed cultures, such as samples collected from the environment and biological reactor systems used by environmental engineers, the spectrophotometer cannot be used to measure the specific growth rate of specific microbial populations. However, several molecular biology-based methods have been described that identify or enumerate distinct microbial populations in mixed culture samples.

The identification and quantification of the abundance of phylogenetically-defined bacterial populations in the environment often is determined using molecular tools targeting 16S rRNA, one of three rRNA molecules in the ribosome. Previously, Oerther and co-workers demonstrated that by targeting the 3' tail of precursor 16S rRNA, the expression and processing of ribosomal RNA could be monitored with fluorescence in situ hybridizations as an indicator of the physiologic state of *Acinetobacter* spp. (Oerther, D. B., et al., *Appl. Environ. Microbiol.*, 2000, 66:2154-2165). U.S. Pat. Nos. 5,770,373; 5,726,021; and 5,712,095 describe methods for identifying chloramphenicol resistant strains of mycobacteria. They describe the typical response of ribosome synthesis to chloramphenicol, but do not describe the use of chloramphenicol or other protein synthesis inhibitors to measure the specific rate of ribosome synthesis.

The growth response of individual cells of bacteria can be determined by measuring the level of pre16S rRNA in individual cells (Stroot, P. G. and Oerther, D. B. *Water Sci. Technol.*, 2003, 47(11):241-250). This measurement of pre16S rRNA in individual cells is possible by using FISH with a probe that targets the 3' end of pre16S rRNA. A new molecular biology method was developed that determines the growth state of an entire bacterial population by determining the level of pre16S rRNA relative to the mature 16S rRNA. Previously, it was demonstrated that the level of pre16S in individual cells of *A. calcoaceticus* is an indication of their growth state (Stroot, P. G. and Oerther, D. B. *Water Sci. Technol.*, 2003, 47(11):241-250). However, this approach was laborious for mixed cultures, since it required a unique pre probe for each specific bacteria of interest. In addition, the pre16S sequence information available to researchers from the Ribosomal Intergenic Spacer Sequence Collection (RISSC), was restricted to the 3' precursor region and the total number of sequences was significantly less than the available 16S rRNA sequence information (Garcia-Martinez, J. et al. *Nucleic Acids Res.*, 2001, 29(1):178-80). Cangelosi and Brabant (Cangelosi, G. A. and Brabant, W. H., *J. of Bacteriol.*, 1997, 179(14):4457-4463) used a reverse transcription method to measure the level of precursor 16S rRNA in cells of *E. coli* that were exposed to chloramphenicol.

It would be advantageous to have available a method that would allow for rapid determination of the specific growth rate of particular microbial populations in a mixed culture.

BRIEF SUMMARY OF THE INVENTION

The present invention concerns a method for determining the specific growth rate of a distinct cell population within a non-homogeneous system, such as a mixed culture, by measuring the specific rate of ribosome synthesis. When used to determine the specific growth rate of a distinct microbial cell population, the method of the invention (also referred to herein as RT-RiboSyn) targets the 16S rRNA and precursor 16S rRNA (pre16S rRNA) by using an oligonucleotide probe that targets a unique stretch of sequence that is found within both RNA molecules. In normal ribosome synthesis, pre16S rRNA is generated through expression of the rrn operons and a subsequent processing step carried out by RNaseIII. The pre16S rRNA is then processed a second time by RNases to generate 16S rRNA. By using a protein synthesis inhibitor, such as chloramphenicol, the processing of the pre16S rRNA is prevented, resulting in accumulation of the pre16S rRNA while maintaining a constant level of 16S rRNA. By collecting samples over time, the rate of pre16S rRNA buildup relative to the 16S rRNA can be measured and used to calculate the specific rate of ribosome synthesis. This is true because the pre16S rRNA represents the pool of newly synthesized ribosomes, while the 16S rRNA represents the ribosomes present prior to the addition of protein synthesis inhibitor. For a constantly growing cell population, the specific growth rate is identical to the specific rate of ribosome synthesis.

The method of the invention may be utilized in research and various industries, such as environmental management (e.g., water and wastewater treatment systems), bioremediation (e.g., to determine optimum conditions for microbial growth), public health (e.g., identification of rapidly growing infectious microbes), and homeland security (e.g., identification of rapidly growing bioterrorism agents). Examples of potential bacterial cell populations of interest include, but are not limited to, *Nitrospira* spp., *Nitrosospira* spp., *Nitrobacter* spp., *Nitrosomonas* spp., *Clostridium* spp., *Bacillus* spp. (such as *Bacillus anthracis*), methanogenic archaea, coliforms (such as *E. coli*), *Salmonella* spp., and *Bacteroides* spp.

Optionally, in the various embodiments of the invention, the method further comprises recording the determined specific growth rate or specific rate of ribosome synthesis of a rapidly growing cell population in physical or electronic media. Preferably, the specific rate of ribosome synthesis and/or the specific growth rate are recorded or otherwise stored as units of synthesis or growth per unit of time. Optionally, the recorded growth or synthesis rate includes an annotation conveying the growth conditions (e.g., culture conditions) under which the determination was made, such as temperature. In one embodiment, the rate of pre16S rRNA buildup relative to the 16S rRNA is measured and input into a computer algorithm that then calculates the specific rate of ribosome synthesis. Optionally, the specific growth rate or the specific rate of ribosome synthesis can be displayed on an output device, such as an analog recorder, teletype machine, typewriter, facsimile recorder, cathode ray tube display, computer monitor, or other computation device. Optionally, the displayed specific growth rate or specific ribosome synthesis rate includes an annotation conveying the growth conditions (e.g., culture conditions) under which the determination was made (such as temperature).

Optionally, in the various embodiments of the invention, the method further comprises carrying out a manipulation of the non-homogeneous system based on the determined specific growth rate or specific ribosome synthesis rate. The manipulation can comprise, for example, a modification of culture conditions or the provision of a signal to induce expression of a polynucleotide of interest by one or more microbial populations within the system. In one embodiment, the manipulation comprises the addition of a substance that alters the metabolic rate of the one or more populations of microbes within the system. For example, the manipulation may comprise the addition of supplements such as carbon, nitrogen, and/or inorganic phosphates, or modification of temperature and/or pH.

Optionally, in the various embodiments of the invention, the method further comprises comparing the specific growth rate of a cell population within the non-homogeneous system, as determined above, to pre-determined growth rate data characterizing cell populations, such as microbial organisms. The pre-determined growth rate data of a cell population may be that specific growth rate observed under particular growth conditions (e.g., culture conditions), such as at a given temperature or at a given cell number or cell density, for example.

Optionally, in the various embodiments of the invention, the method further comprises introducing a test agent to the non-homogeneous system, or a sample thereof, before, during, or after introduction of the protein synthesis inhibitor, in order to determine whether the test agent exerts a biological effect on the microbes. The test agent may be a member of a combinatorial library, for example. In one embodiment, the method includes contacting the non-homogeneous system, or a sample thereof, with one or more members of a library of agents for the purpose of monitoring the effect on specific growth rate. Optionally, the method further comprises comparing the specific growth rate of a particular microbial population within the non-homogeneous system before and after introduction of the test agent. The particular microbial population may be one that is determined to be rapidly growing in the presence or absence of the test agent, for example.

BRIEF DESCRIPTION OF THE SEQUENCES

Figure 1:
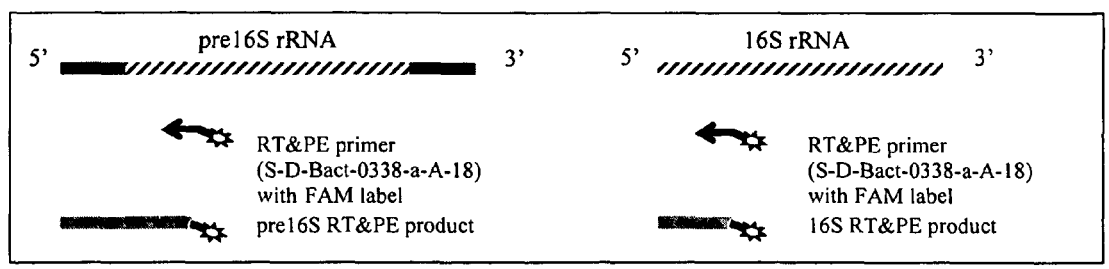
FIG. 1 shows a schematic of the reverse transcription and primer extension (RT&PE) method.

SEQ ID NO:1 is an oligonucleotide primer that can be used according to the present invention.

SEQ ID NO:2 is an oligonucleotide primer that can be used according to the present invention.

DETAILED DESCRIPTION OF THE INVENTION

The method of the invention (also referred to herein as RT-RiboSyn) measures the specific rate of ribosome synthesis for a specific target cell population, such as a microbial cell population. Chloramphenicol or another suitable protein synthesis inhibitor is added to a non-homogeneous system, such as a mixed culture sample, in an amount effective to reduce and, preferably, completely inhibit further pre16S processing. Sub-samples are collected at defined times. The sub-samples can be stored appropriately at −80° C. RNA is extracted and purified prior to reverse transcription and primer extension (RT&PE) using a fluorescently-labeled primer that targets the specific microbial population of interest. The two RT&PE products can then be analyzed by capillary electrophoresis, which separates them and allows for measurement of length and fluorescent intensity. In this manner, the ratio of the pre16S and 16S RT&PE products (pre16S/16S) can be determined for each sample. A simple analysis of these pre16S/16S reveals the ribosome doubling time, which in turn, can be used to calculate the specific rate of ribosome synthesis. Using a high performance liquid chromatography (HPLC) apparatus equipped with a fragment collector, the method of the invention is capable of identifying members of a specific microbial population that are rapidly growing relative to one or more other populations within the mixed culture. This is possible by collecting the pre16S RT&PE product of interest and using polymerase chain reaction (PCR) to amplify a portion of the pre16S RT&PE product. This PCR product can be sequenced using conventional methods and tentatively identified by comparison with the 10,000+16S rRNA gene sequences that are publicly available (e.g., on databases such as GenBank (NCBI-National Center for Biotechnology Information); EMBL (European Molecular Biology Laboratory); DDBJ (DNA Database of Japan); Pathema; CMR (Comprehensive Microbial Resource) databases; and TIGR (The Institute for Genomic Research) databases; RDP-II (Ribosomal Database Project-II; and ATCC (American Type Culture Collection).

RT-RiboSyn measures the specific rate of ribosome synthesis for a specific cell population of interest within a mixed culture composed of multiple (two or more) populations of cells (such as microbes). For an actively growing (or non-growing) cell population, the specific rate of ribosome synthesis is identical to the specific growth rate of the cell population. With the RT-RiboSyn method of the invention, researchers can measure the specific growth rate of distinct microbial populations in non-homogeneous (mixed) systems, such as biological reactor systems or environmental samples. In addition, the method of the invention provides the ability to identify members of a distinct cell population (e.g., microbial cell population) that are rapidly growing.

In one embodiment, the method of the invention comprises: exposing a mixed sample to chloramphenicol or other suitable protein synthesis inhibitor, optionally, in the existing environmental conditions; over time, collecting samples from the mixed culture that has been exposed to the protein synthesis inhibitor; and measuring the rate of precursor (pre) 16S rRNA accumulation (e.g., using a molecular biology based method, such as a reverse transcription method ex situ). The specific growth rate for a specific target cell population can be determined by its rate of pre16S rRNA accumulation. Distinct cell populations can be targeted exclusively by using oligonucleotide probes or primers that target the common signature sequence information within the pre16S rRNA and mature 16S rRNA. Various methods for designing suitable probes or primers are available (see, for example, Ashelford K. E. et al., "PRIMROSE: a computer program for generating and estimating the phylogenetic range of 16S rRNA oligonucleotide probes and primers in conjunction with the RDP-II database", *Nucleic Acids Research*, 2002, 30(15):3481-3489, and databases/tools available through probeBase, an online resource for rRNA-targeted oligonucleotide probes (University of Vienna, Department of Microbial Ecology); each of which are incorporated herein by reference in their entirety).

The method of the invention measures the increase of pre16S/16S of a specific target cell population. The method can be carried out ex situ using a reverse transcription and primer extension method to analyze the RNA extracted from a series of samples treated with chloramphenicol or other protein synthesis inhibitor. Preferably, a single fluorescently labeled primer that is specific for a microbial population and targets an interior region of both pre16S and 16S rRNA is employed. The pre16S/16S can be determined by separating the RT&PE products, which have different lengths, and measuring the fluorescent intensity of each. RT-RiboSyn has the potential to identify members of a microbial population (species or strain) that are growing rapidly relative to the other members present.

A schematic of the reverse transcription and primer extension (RT&PE) method is shown in FIG. 1. In this figure, the primary structure of each target molecule and the RT&PE product derived from each molecule is shown. In addition, the precursor regions of the pre16S rRNA are shown as black. The primer, S-D-Bact-0338-a-A-18, was chosen because it targets a site that is found in precursor and mature 16S rRNA for all bacteria. The primer was fluorescently labeled with FAM for detection analysis by capillary gel electrophoresis. The two RT&PE products from a pure culture, shown as gray, are distinguished by differences in length. For an environmental sample, such as activated sludge, the RT&PE method was modified to gather growth state information for a specific microbial population by using a primer that targets that specific microbial population.

The RT&PE method detects a growth response in specific cell populations by monitoring the ratio of the pre16S RT&PE product to the 16S RT&PE product, which is also the ratio of the precursor 16S rRNA to the mature 16S rRNA (pre16S/16S). The results from the RT&PE and FISH methods were found to be consistent; however, both methods were unable to differentiate between non-growing cells and rapidly growing cells for low pre16S/16S. The solution to this problem is to use the RT&PE method to measure the specific rate of ribosome synthesis by monitoring the change of the pre16S/16S over time for a culture exposed to chloramphenicol or other protein synthesis inhibitor. Preferably, like chloramphenicol, the inhibitor inhibits the secondary processing of precursor 16S rRNA, but does not inhibit the production of precursor 16S rRNA (Tomlins, R. I. and Ordal, Z. J. *J. Bacteriol.*, 1971, 107(1):134-42). In addition to chloramphenicol, lincomycin and erythromycin are ribosomally active antibiotics that block the formation of peptide bonds by binding at or near the aminoacyl tRNA binding site on the large ribosomal subunit. Bacteriostatic derivatives of these agents, such as aminoacyl and peptidyl analogs of chloramphenicol, which permit production of pre16S rRNA but inhibit its secondary processing, may be used (see, for example, Michelinaki, M. et al., *Molecular Pharmacology*, 1997, 51:139-146; Coutsogeorgopoulos C et al., "Requirements for Inhibition of Peptide Bond Formation by Analogs of Chloramphenicol," in *Progress in Chemotherapy of the 8$^{th}$ International Congress of Chemotherapy* (G. K. Daikos, ed.), 1974, Vol. 1, Hellenic Society of Chemotherapy, Athens, 417-420; McFarlan, S. C., and R. Vince, *Biochem. Biophys. Res. Commun.*, 1984, 122:748-754; and Drainas, D. et al., *J. Med. Chem.*, 1993, 36:3542-3545; Vince R. et al., *Antimicrobial Agents and Chemotherapy*, 1975, 8(4):439-443; Cannon M. et al., *J. Antimicrobial Chemotherapy*, 1990, 26:307-317; each of which are incorporated by reference in their entirety). Thiamphenicol, a chloramphenicol derivative in which the nitro group is replaced with a sulfonomethyl, or florfenicol, a chloramphenicol derivative in which fluorine replaces chlorine, can be used. Some derivatives, such as chloramphenicol succinate, exhibit increased water solubility compared to the parent compound. Structural isomers or steroisomers may be used. Methods for the stereoselective synthesis of aminodiols, such as chloramphenicol, fluoramphenicol, and thiamphenicol are known in the art (Mateius, C. R. and F. Coleho, *J. Braz. Chem. Soc.*, 2005, 16(3A):386-396).

The method of the invention measures the rate of increase of the pre16S rRNA relative to the 16S rRNA (pre16S/16S) in cells that are exposed to chloramphenicol or other protein synthesis inhibitor. The chloramphenicol inhibits the secondary processing of pre16S rRNA, which results in a buildup of the pool of pre16S rRNA relative to the 16S rRNA. When cells are exposed to a protein synthesis inhibitor such as chloramphenicol, the cellular level of 16S rRNA represents the existing ribosome levels, while the increasing level of pre16S rRNA represents newly synthesized ribosomes. By correcting for the 16S rRNA and initial pre16S/16S, the ribosome doubling time and, therefore, the specific rate of ribosome synthesis can be calculated. Unlike Cangelosi and Brabant's approach (Cangelosi, G. A. and Brabant, W. H. *J. of Bacteriol.*, 1997, 179(14):4457-4463), the RT-RiboSyn method can target specific microbial populations by taking advantage of the extensive databases for oligonucleotide probes that target specific sequence within the mature and precursor 16S rRNA (Loy, A. et al. *Nucleic Acids Res.*, 2003, 31(1):514-6). The method of the invention has tremendous potential for environmental engineers and scientists that desire to determine how fast distinct cell populations are growing.

The method of the invention has an additional, powerful feature: the ability to identify fast growing members of a distinct microbial population from a sample collected from a biological reactor system. A capillary gel electrophoresis system coupled with a fragment collector (WAVE instrument by Transgenomic, Inc.) can collect pre16S RT&PE products for identification by conventional PCR and cloning methods.

The various methods employed in the preparation of the plasmids and transformation of host organisms are well known in the art and are described, for example, in U.S. Pat. Nos. 5,011,909 and 5,130,253. These patents are incorporated herein by reference in their entirety. These procedures are also described in Maniatis, et al. (1982) *Molecular Cloning: A Laboratory Manual*, Cold Spring Harbor Laboratory, New York. Thus, it is within the skill of those in the genetic engineering art to extract DNA from its source, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

Optionally, in the various embodiments of the invention, the method further comprises recording the determined specific growth rate or specific rate of ribosome synthesis of a rapidly growing cell population in physical or electronic media. Preferably, the specific rate of ribosome synthesis and/or the specific growth rate are recorded or otherwise stored as units of synthesis or growth per unit of time. Optionally, the recorded growth or synthesis rate includes an annotation conveying the growth conditions (e.g., culture conditions) under which the determination was made, such as temperature. In one embodiment, the rate of pre16S rRNA buildup relative to the 16S rRNA is measured and input into a computer algorithm that then calculates the specific rate of ribosome synthesis. Optionally, the specific growth rate or the specific rate of ribosome synthesis can be displayed on an output device, such as an analog recorder, teletype machine, typewriter, facsimile recorder, cathode ray tube display, computer monitor, or other computation device. Optionally, the displayed specific growth rate or specific ribosome synthesis rate includes an annotation conveying the growth conditions (e.g., culture conditions) under which the determination was made (such as temperature).

Optionally, in the various embodiments of the invention, the method further comprises carrying out a manipulation of the non-homogeneous system based on the determined specific growth rate or specific ribosome synthesis rate. The manipulation can comprise, for example, a modification of culture conditions or the provision of a signal to induce expression of a polynucleotide of interest by one or more microbial populations within the system. In one embodiment, the manipulation comprises the addition of a substance that alters the metabolic rate of the one or more populations of microbes within the system. For example, the manipulation may comprise the addition of supplements such as carbon, nitrogen, and/or inorganic phosphates, or modification of temperature and/or pH.

Optionally, in the various embodiments of the invention, the method further comprises comparing the specific growth rate of a cell population within the non-homogeneous system, as determined above, to pre-determined growth rate data characterizing cell populations, such as microbial organisms. The pre-determined growth rate data of a cell population may be that specific growth rate observed under particular growth conditions (e.g., culture conditions), such as at a given temperature or at a given cell number or cell density, for example.

Optionally, in the various embodiments of the invention, the method further comprises introducing a test agent to the non-homogeneous system, or a sample thereof, before, during, or after introduction of the protein synthesis inhibitor, in order to determine whether the test agent exerts a biological effect on the microbes. The test agent may be a member of a combinatorial library, for example. In one embodiment, the method includes contacting the non-homogeneous system, or a sample thereof, with one or more members of a library of agents for the purpose of monitoring the effect on specific growth rate. Optionally, the method further comprises comparing the specific growth rate of a particular microbial population within the non-homogeneous system before and after introduction of the test agent. The particular microbial population may be one that is determined to be rapidly growing in the presence or absence of the test agent, for example.

The cells assayed for specific growth rate in accordance with the method of the invention may be genetically modified (e.g., recombinant) or non-genetically modified. If a vector is used to genetically modify the cell, it may be in the form of a plasmid, a viral particle, a phage, etc. Transformed (genetically modified) cells can be cultured in conventional nutrient media modified as appropriate for activating promoters, selecting transformants/transfectants or amplifying the sub-unit-encoding polynucleotide. The culture conditions, such as temperature, pH and the like, generally are similar to those previously used with the host cell selected for expression, and will be apparent to those of skill in the art.

The terms "recombinant host cells", "host cells", "cells", "cell lines", "cell cultures", and other such terms refer to prokaryotic or eukaryotic cells which can be, or have been, used as recipients for recombinant vectors or other transfer DNA, immaterial of the method by which the DNA is introduced into the cell or the subsequent disposition of the cell. Thus, the cells subjected to the method of the invention can be, for example, any bacterial cells (e.g., Gram-positive, Gram-negative, those not lending themselves to Gram stain, aerobic, anaerobic, etc.), yeast cells, vertebrate cells (such as human or non-human mammalian cells), invertebrate cells, etc. The terms include the progeny of the original cell that has been transfected. The term "recombinant" when used with reference to a cell, or polynucleotide, polypeptide, or vector, indicates that the cell, polynucleotide, polypeptide or vector, has been modified by the introduction of a heterologous nucleic acid or amino acid or the alteration of a native nucleic acid or amino acid, or that the cell is derived from a cell so modified. A polypeptide of interest can be encoded by a gene that is part of the cell's genome, but for which regulatory sequences have been modified to provide increased levels of expression. Thus, recombinant cells can express genes that are not found within the native (non-recombinant) form of the cell or express native genes that are otherwise abnormally expressed, under expressed or not expressed at all. The prokaryotic or eukaryotic cells subjected to the method of the invention may be recombinant cells, un-modified cells, or a mixture thereof.

The term "genetic modification" as used herein refers to the stable or transient alteration of the genotype of a cell by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides. A translation initiation codon can be inserted as necessary, making methionine the first amino acid in the sequence. The terms "transfection" and "transformation" are used interchangeably herein to refer to the insertion of an exogenous polynucleotide into a host cell, irrespective of the method used for the insertion, the molecular form of the polynucleotide that is inserted, or the nature of the cell (e.g., prokaryotic or eukaryotic). The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome.

Examples of microorganisms that may be assayed for cell growth rate in accordance with the method of the invention include, but are not limited, to those of importance to wastewater and waste treatment processes (e.g., nitrifying bacteria, phosphorus accumulating organisms, and methanogens), public health (e.g., coliforms and bioterrorism agents) and food safety (e.g., botulism). Examples of potential bacterial cells of interest include, but are not limited to, *Nitrospira* spp., *Nitrosospira* spp., *Nitrobacter* spp., *Nitrosomonas* spp., *Clostridium* spp., *Bacillus* spp. (such as *Bacillus anthracis*), methanogenic archaea, coliforms (such as *E. coli*), *Salmonella* spp., and *Bacteroides* spp.

The medium used to cultivate the cells may be any conventional medium suitable for growing the populations of cells in question and, optionally, obtaining expression of a gene of interest. Cells can be grown under amenable culture conditions, i.e., appropriate conditions of temperature, pH, humidity, oxygen, and nutrient availability including carbon/energy sources. Suitable media are available from commercial suppliers or may be prepared according to published protocols (e.g., as described in catalogues of the American Type Culture Collection).

Gene products secreted from the cell populations in the mixed culture or samples derived there from may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

As used herein, the term "protein synthesis inhibitor" is intended to refer to bacteriostatic agents that inhibit the secondary processing of precursor 16S rRNA, but do not inhibit the production of precursor 16S rRNA. For example, chloramphenicol, lincomycin, and erythromycin, are ribosomally active antibiotics that block the formation of peptide bonds by binding at or near the aminoacyl tRNA binding site on the large ribosomal subunit. After some time, the previously synthesized peptidyl tRNA is released and hydrolyzed. The ribosomal subunits are then released from the mRNA and are free to rejoin other mRNA molecules to start another abortive cycle. This leads to a truncated version of the ribosome cycle. Thus, these drugs inhibit protein synthesis at the chain elongation step, leading to premature association of the active complex. As a result, when these antibiotics are withdrawn, many free ribosomes are present and ready to resume normal protein synthesis. This explains why the action of these drugs is reversible and why these antibiotics are bacteriostatic instead of bacteriocidal. The protein synthesis inhibitor may be one that inhibits the secondary processing of rRNA in prokaryotic cells, eukaryotic cells, or both cell types.

As used herein, the terms "non-homogeneous system", "non-homogeneous sample", "mixed system", and "mixed sample" are interchangeable and refer to a mixture of two or more cell populations (such as microbial populations). The non-homogeneous system may be, for example, a cell culture, human or animal tissue (such as flesh, blood, saliva, semen, vaginal secretion, urine, tears, perspiration, extracellular fluid, etc.), or an environmental sample, such as water, soil, or sludge. The non-homogeneous system can be a small-scale or large scale fermentation. The non-homogeneous system may be contained within a test tube, culture vessel, fermentation tank, multi-well plate, or any other container or supporting substrate. The non-homogeneous system may be in any physical state (e.g., solid, liquid, vapor).

As used herein, the terms "population" and "cell population" (e.g., target cell population) are intended to refer to a distinguishable group of eukaryotic or prokaryotic cells, such as a genus, species or strain of microorganism. A population can differ from other populations by phylogenetic profile or by some other detectable genotype and/or phenotype. Using the method of the invention, populations can be distinguished from each other based on specific growth rate and length heterogeneity of the pre16S RT&PE products. A population can comprise two or more sub-populations that differ from each other by some detectable genotype and/or phenotype. A non-homogeneous system such as a mixed culture can be so small as to comprise two populations or can be larger, e.g., $10^{12}$ populations. In some embodiments, a mixed culture is between five and 20 different populations, as well as up to hundreds or thousands of different populations. Those skilled in the art can readily determine a suitable size and diversity of a population sufficient for a particular application.

The terms "microbe" and "microbial cell" are inclusive of all prokaryotic microorganisms with a protein synthesis pathway susceptible to suppression by the protein synthesis inhibitor utilized in accordance with the invention. The microbe may be pathogenic or non-pathogenic.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state.

As used in this specification, the singular forms "a", "an", and "the" include plural reference unless the context clearly dictates otherwise. Thus, for example, a reference to "a microorganism" includes more than one such microorganism. A reference to "a cell" includes more than one such cell, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

Following is an example that illustrates materials, methods, and procedures for practicing the invention. The example is illustrative and should not be construed as limiting. The preliminary experimental results described provide evidence that the RT-RiboSyn method can be used to measure the specific rate of ribosome synthesis within microbial cells, which is identical to the specific growth rate.

EXAMPLE 1

Figure 2:
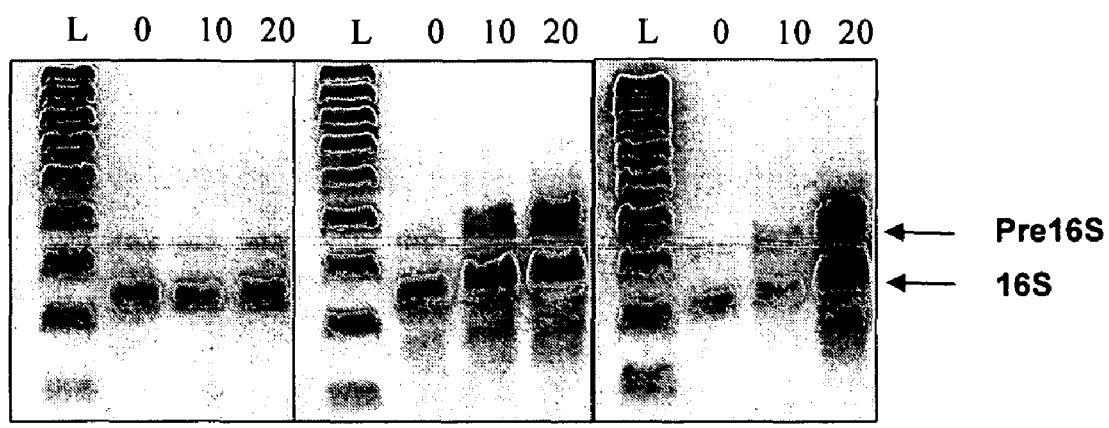
FIG. 2 shows agarose gel electrophoresis images for *A. calcoaceticus* stationary phase culture at 30° C. (gel A), mid-log phase culture at 25° C. (gel B), and mid-log phase culture at 30° C. (gel C). A 100 bp ladder is provided for size estimation. The lanes correspond to 0, 10, and 20 minutes of exposure to chloramphenicol. Arrows indicate the RT&PE products (16S and Pre16S).

RT-RiboSyn Measures the Specific Rate of Ribosome Synthesis for *A. calcoaceticus* Cultures at Three Different Specific Growth Rates In a simple experiment, the specific rate of ribosome synthesis was measured for *A. calcoaceticus* cultured at different specific growth rates. In order to produce cultures with distinct specific growth rates during mid-log phase, cultures of *A. calcoaceticus* were incubated in 100 mL of nutrient broth at 25 and 30° C. The specific growth rate was calculated with absorbance (686 nm) measurements for both cultures. For both cultures, a 12-mL sample was removed at mid-log phase (Absorbance=~0.50) and stationary phase (30° C. only) and transferred to another flask and chloramphenicol (final 20 mg/L) was added immediately. Three sub-samples (2 mL) were collected from each culture after 0, 10, and 20 minutes of exposure to chloramphenicol. Each of the three sub-samples was promptly centrifuged (10,000 rpm for 5 minutes) and the supernatant decanted prior to storage at −80° C. The RNA was extracted from all samples and cleaned using methods described previously (RNAqueous by AMBION, followed by RNAseA treatment (SIGMA)). A new RT&PE method was used to determine the ratio of RT&PE products derived from the precursor and mature 16S rRNA. The RT&PE products were stained with SYBR Green I and both products were separated and analyzed by agarose gel electrophoresis, as shown in FIG. 2. The pre16S and 16S RT&PE product sizes are approximately 450 nt and 350 nt, respectively. These sizes are consistent with predicted sizes based on the genome sequence information for a closely related species. A clear difference in the pre16S/16S is evident when comparing the series of samples for the stationary phase culture and the two mid-log phase cultures. No significant increase in the pre16S/16S was observed for the stationary phase culture (FIG. 2, gel A), which is consistent with the non-growth condition (Gausing, K. *J. Mol. Biol.*, 1977, 115 (3):335-54). For the mid-log phase cultures (FIG. 2, gels A and B), a rapid increase in the pre16S/16S is observed as the culture is exposed to the chloramphenicol for longer periods. This indicates a high specific rate of ribosome synthesis for these actively growing cultures.

For each gel image, the pre16S/16S ratios were determined by using the Kodak analysis software to determine areas (pixels) of the bands in each lane, multiplied by the average intensity of each band. Doubling times were determined by correcting for the initial pre16S/16 and then using a linear regression to determine an equation. This equation was used to determine the time required for pre16S/16S to equal one (doubling). This doubling time was then used to calculate the specific rate of ribosome synthesis by dividing ln(2) by the doubling time. For each culture, the specific growth rate and the specific rate of ribosome synthesis are shown in Table 1. Clearly, the specific rates of ribosome synthesis are consistent with the specific growth rates for each culture. With the use of capillary gel electrophoresis, a more accurate measurement of the pre16S/16S is possible through the use of a fluorescence detector.

TABLE 1

A comparison of the specific growth rate and specific rate of ribosome synthesis for *A. calcoaceticus* at stationary phase and mid-log phase.

|  | Specific growth rate (hr$^{-1}$) | Specific rate of ribosome synthesis (hr$^{-1}$) |
|---|---|---|
| Stationary Phase | 0.02 | 0.04 |
| Mid-log Phase; T = 25° C. | 0.60 | 0.82 |
| Mid-log Phase; T = 30° C. | 1.04 | 1.15 |

Figure 3A:
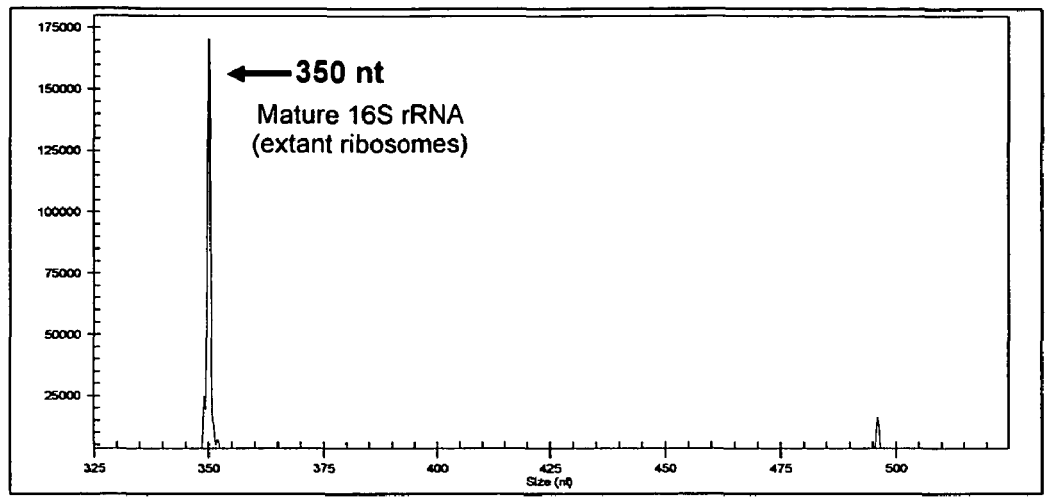
FIGS. 3A and 3B show electropherograms of RT-RiboSyn products derived from *A. calcoaceticus* incubated in nutrient broth at 25° C. after exposure to chloramphenicol for zero minutes (FIG. 3A) and 20 minutes (FIG. 3B). The WellRed-labeled Eub0338 primer (5' GCT GCC TCC CGT AGG AGT 3'; SEQ ID NO:1) was used.
Figure 3B:
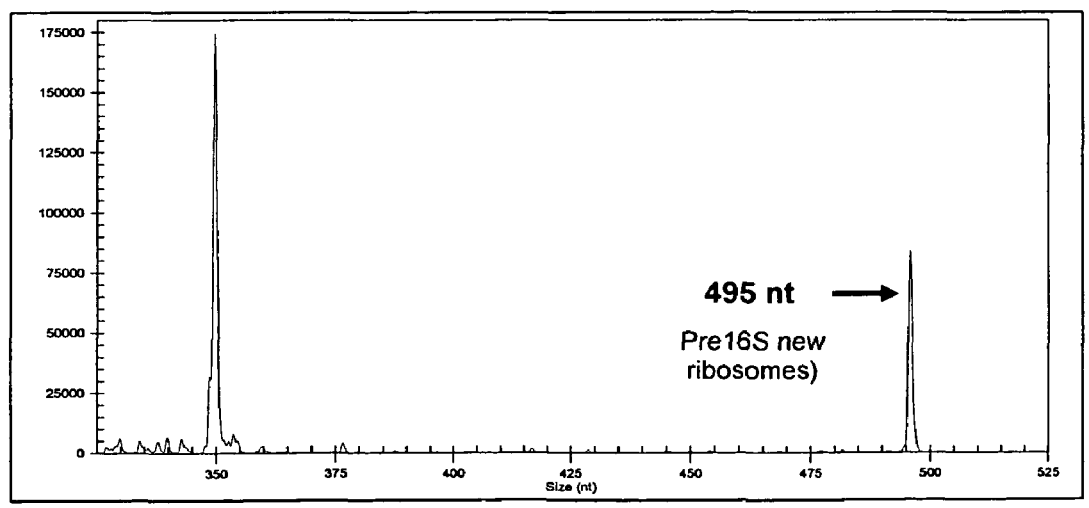

Representative results of the RT&PE products derived from the Eub0338 primer (5' GCT GCC TCC CGT AGG AGT 3'; SEQ ID NO:1) and a culture of *Acinetobacter calcoaceticus* are shown in the electropherograms in FIG. 3A and FIG. 3B. The peak at 350 nt in length represent the mature 16S rRNA, or extant ribosomes, and the peak at 495 nt represents the pre16S rRNA, or new ribosomes. The peaks derived from *A. calcoaceticus* 16S rRNA and pre16S rRNA were previously reported (Stroot, P. G. "Novel transcription method confirms growth inhibition of bacteria exposed to domestic wastewater" Ph.D. Dissertation, University of Cincinnati, 2004 which is incorporated herein by reference in its entirety) as 351 and 494 nt, respectively. These slight differences in size are likely due to a different method of analysis. As shown, the relative height of the peak for the pre16S rRNA as compared to the 16S rRNA peak increases with time.

The rate of increase of the peak ratios over time were used to determine the ribosome doubling time. As stated previously, the cell doubling time is equivalent to the ribosome doubling time for cells that are doubling at a constant rate. The cell doubling time can then be used to calculate the specific growth rate for the culture. A comparison of the specific growth rate as determined by the traditional method (i.e., spectrophotometer) and the RT-RiboSyn method is shown in Table 2.

TABLE 2

Measured specific growth rates of *A. calcoaceticus* from the use a spectrophotometer and the RT-RiboSyn method.

| | | μ (hr$^{-1}$) | | |
|---|---|---|---|---|
| Primer | Culture Temperature | Spectro-photometer | RT-RiboSyn | % difference |
| Eub0338 | 25° C. | 0.38 | 0.44 | 14% |
| Eub0338 | 30° C. | 0.55 | 0.63 | 13% |
| Eub0338 | 30° C. (stationary) | 0.01 | 0.04 | 75% |
| Acin0659 | 30° C. | 0.55 | 0.71 | 23% |

For the mid-log growth phase samples with the Eub0338 primer (5' GCT GCC TCC CGT AGG AGT 3'; SEQ ID NO:1), the specific growth rates as calculated using the RT-RiboSyn method are in close (within 14% difference) agreement with those calculated from the spectrophotometer data. For the genus specific primer, Acin0659 (5' CTG GAA TTC TAC CAT CCT CTC CCA 3'; SEQ ID NO:2), the specific growth rate calculated from the RT&PE products generated are within 23% of those calculated by the traditional method, which is in good agreement with the results from the Eub0338 primer. For both primers, the specific growth rates determined by the RT-RiboSyn method are greater than those determined by optical density measurements. Earlier work (Gausing, K. *J. of Molec. Biol.*, 1977, 3:335-354) has shown that newly transcribed rRNA in *Escherichia coli* is degraded at rates of about 10% and 70% for high (μ=1.4 h$^{-1}$) and low (μ=0.1 hr$^{-1}$) cell specific growth rates, respectively. The rate of rRNA degradation for the higher cell specific growth rate could account for the difference between the specific growth rates as determined by spectrophotometer and RT-RiboSyn. It has been shown that chloramphenicol completely prevents pre16S rRNA degradation under all conditions in *E. coli* (Cangelosi, G. A. and Brabant, W. H. *J. Bacteriol.*, 1997, 179:4457-4463). Assuming this behavior holds true for *A. calcoaceticus*, degradation of 16S rRNA while accumulating pre16S rRNA will increase the specific growth rate as determined by RT-RiboSyn when compared to traditional methods. For the stationary phase sample, a large discrepancy exists between the two measurements and may represent a limitation of the RT-RiboSyn method. Low growth rates (at around μ=0.1 hr$^{-1}$) have been shown to have rRNA degradation rates of 70%, which could account for the large discrepancy between the two measured specific growth rates (Gausing, K. *J. of Molec. Biol.*, 1977, 3:335-354). More importantly, lengthy doubling times were calculated from both growth rate measurement methods, indicating that the cultures are not growing.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for determining the specific growth rate of a target cell population within a non-homogeneous system, comprising determining the specific rate of ribosome synthesis in the target cells of the system, and correlating the specific rate of ribosome synthesis to the specific growth rate of the target cell population, wherein said determining step comprises:
   (a) exposing the target cells in the non-homogeneous system to a compound that inhibits secondary processing of precursor 16S rRNA without inhibiting production thereof;
   (b) collecting and preserving samples comprising target cells from the non-homogeneous system over time;
   (c) measuring the ratio of precursor 16S rRNA to mature 16S rRNA in the preserved samples; and
   (d) determining the specific rate of ribosome synthesis in the target cells by determining the change in the ratio of the precursor 16S rRNA to mature 16S rRNA over the time of exposure of the target cells to the inhibitory compound; and
wherein the non-homogeneous system is a biological sample selected from the group consisting of blood, saliva, semen, vaginal secretion, urine, tears, perspiration, and extracellular fluid.

2. The method of claim 1, wherein said measuring of step (c) is carried out by reverse transcription ex situ.

3. The method of claim 2, wherein an oligonucleotide probe or primer is used to target a signature sequence that is present in both the precursor 16S rRNA and mature 16S rRNA of the target cell population.

4. The method of claim 2, wherein the compound is selected from the group consisting of chloramphenicol, lincomycin, and erythromycin.

5. The method of claim 2, wherein the compound is a chloramphenicol derivative selected from the group consisting of thiamphenicol, florfenicol, chloramphenicol succinate, and fluoramphenicol.

6. The method of claim 2, wherein the compound comprises chloramphenicol.

7. The method of claim 1, wherein the target cell of the target cell population is a pathogen.

8. The method of claim 1, wherein the target cell population has a higher growth rate relative to other cell populations in the non-homogeneous system under a specific growth condition.

9. The method of claim 1, further comprising recording the determined specific growth rate or specific rate of ribosome synthesis of the target cell population in physical or electronic media.

10. The method of claim 2, wherein said determining of step (d) comprises entering the ratio of precursor 16S rRNA to mature 16S rRNA over the time of exposure of the target cells to the inhibitory compound into a computer algorithm that calculates the specific rate of ribosome synthesis.

11. The method of claim 1, further comprising comparing the specific growth rate of the target cell population with pre-determined growth rate data characterizing cell populations.

12. The method of claim 1, further comprising comparing the specific growth rate of the target cell population within the non-homogeneous system before and after introduction of a test agent.

13. The method of claim 1, wherein the target cell of the target cell population is a microbial cell.

14. The method of claim 1, wherein the target cell population is selected from the group consisting of *Nitrospira* spp., *Nitrosospira* spp., *Nitrobacter* spp., *Nitrosomonas* spp., *Clostridium* spp., *Bacillus* spp., methanogenic archaea, coliform, *Salmonella* spp., and *Bacteroides* spp.

15. The method of claim 1, wherein the target cell population comprises genetically modified cells.

16. The method of claim 1, wherein the non-homogeneous system comprises a plurality of cell populations.

* * * * *